(12) United States Patent
Kim et al.

(10) Patent No.: US 10,570,561 B2
(45) Date of Patent: Feb. 25, 2020

(54) SIZING AGENT FOR CARBON FIBER, CARBON FIBER WITH IMPROVED INTERFACIAL ADHESION, POLYMERIZATION REACTION TYPE CARBON FIBER-REINFORCED POLYMER COMPOSITE MATERIAL USING SAME, AND PRODUCTION METHOD THEREFOR

(71) Applicant: KOREA INSTITUTE OF MACHINERY & MATERIALS, Daejeon (KR)

(72) Inventors: Sangwoo Kim, Goyang-si (KR); Jin Woo Yi, Changwon-si (KR); Dong Gi Seong, Changwon-si (KR); Moon-Kwang Um, Changwon-si (KR); Kangeun Lee, Changwon-si (KR); Taehoon Park, Changwon-si (KR); Youngseok Oh, Gimhae-si (KR)

(73) Assignee: KOREA INSTITUTE OF MACHINERY & MATERIALS, Daejeon (KR)

( * ) Notice: Subject to any disclaimer, the term of this patent is extended or adjusted under 35 U.S.C. 154(b) by 0 days.

(21) Appl. No.: 16/347,342

(22) PCT Filed: Nov. 25, 2016

(86) PCT No.: PCT/KR2016/013694
§ 371 (c)(1),
(2) Date: May 3, 2019

(87) PCT Pub. No.: WO2018/097362
PCT Pub. Date: May 31, 2018

(65) Prior Publication Data
US 2019/0284751 A1   Sep. 19, 2019

(30) Foreign Application Priority Data

Nov. 24, 2016  (KR) .................. 10-2016-0157578

(51) Int. Cl.
*D06M 13/395* (2006.01)
*C08K 9/04* (2006.01)
(Continued)

(52) U.S. Cl.
CPC ......... *D06M 13/395* (2013.01); *C07D 223/10* (2013.01); *C08J 5/06* (2013.01);
(Continued)

(58) Field of Classification Search
CPC .................................................. D06M 13/395
See application file for complete search history.

(56) References Cited

U.S. PATENT DOCUMENTS

| 5,116,958 A | 5/1992 | Liechti et al. |
| 5,239,046 A | 8/1993 | Lubowitz et al. |

(Continued)

FOREIGN PATENT DOCUMENTS

| JP | 2001020181 | 1/2001 |
| JP | 2014-231588 | 12/2014 |

(Continued)

*Primary Examiner* — Vickey Nerangis
(74) *Attorney, Agent, or Firm* — Lex IP Meister, PLLC

(57) ABSTRACT

The present invention relates to a sizing agent for carbon fibers, a carbon fiber with improved interfacial adhesion, a polymerization reaction type carbon fiber-reinforced polymer composite material using the same, and a production method therefor and, more specifically, to a sizing agent for carbon fibers, comprising a phenoxy resin and a block isocyanate compound prepared through a reaction of ε-caprolactam with one of two isocyanate groups of a diisocyanate compound, and the production of a carbon fiber with improved interfacial adhesion using the same, a polymerization reaction type carbon fiber-reinforced polymer composite material using the carbon fiber with improved interfacial adhesion, and a production method therefor.

11 Claims, 12 Drawing Sheets

(51) Int. Cl.
*C07D 223/10* (2006.01)
*C08J 5/06* (2006.01)
*D06M 14/36* (2006.01)
*D06M 101/40* (2006.01)

(52) U.S. Cl.
CPC ............... *C08K 9/04* (2013.01); *D06M 14/36* (2013.01); *C08J 2377/04* (2013.01); *D06M 2101/40* (2013.01)

(56) References Cited

U.S. PATENT DOCUMENTS

2006/0289842 A1* 12/2006 Craig ..................... C08K 3/08
 252/514
2014/0296377 A1  10/2014 Tadepalli et al.

FOREIGN PATENT DOCUMENTS

| KR | 10-19890006917 | 6/1989 |
| KR | 10-1052131 | 7/2011 |
| KR | 10-1482452 | 1/2015 |
| KR | 10-1498559 | 3/2015 |
| KR | 10-1530754 | 6/2015 |

* cited by examiner

SIZING AGENT FOR CARBON FIBER, CARBON FIBER WITH IMPROVED INTERFACIAL ADHESION, POLYMERIZATION REACTION TYPE CARBON FIBER-REINFORCED POLYMER COMPOSITE MATERIAL USING SAME, AND PRODUCTION METHOD THEREFOR

BACKGROUND OF THE INVENTION

1. Field of the Invention

The present invention relates to a sizing agent for carbon fibers, a carbon fiber with improved interfacial adhesion, a polymerization reaction type carbon fiber-reinforced polymer composite material using the same, and a production method thereof.

More specifically, the present invention relates to a sizing agent for carbon fibers, comprising a phenoxy resin and a block isocyanate compound prepared through a reaction of ε-caprolactam with one of two isocyanate groups of a diisocyanate compound, and the production of a carbon fiber with improved interfacial adhesion using the same, a polymerization reaction type carbon fiber-reinforced polymer composite material using the carbon fiber with improved interfacial adhesion, and a production method thereof.

This application claims benefit of Korean Patent application 10-2016-0157578 filed on Nov. 24, 2016, the contents of which are incorporated herein by reference.

2. Description of the Related Art

A composite material is a general term for the material having the characteristics that cannot be obtained from a single material, which are acquired by combining heterogeneous and different materials, and having excellent properties suitable for the requirements. Among those composite materials, there is a polymer composite material in which a polymer material having a high specific strength (tensile strength/density) and a specific stiffness (elastic modulus/density) is used as a matrix.

A fiber reinforced polymer composite material includes a fiber layer conjugated with a matrix material such as a polymer resin. This fiber can reinforce the matrix to withstand most of the load sustained by the composite, but the matrix sustains a small fraction of the load sustained by the composite and transfers the load from the broken fiber to the intact fiber. In this way, the composite material can sustain a greater load than the matrix or fiber alone can sustain.

Carbon fiber reinforced plastic, which is a kind of composite material, has been used for a long time in a variety of applications due to its excellent mechanical properties, chemical resistance and light weight. Recently, the carbon-fiber reinforced plastic has gotten a lot of attention in the field of automotive industry because leading companies in electric vehicles mass-produce electric vehicles, mostly made of the carbon fiber reinforced plastic. Accordingly, many studies and advances in structural composite materials have been made worldwide.

In this carbon fiber reinforced composite material, the most important factors affecting the strength of the composite material are the interfacial binding strength between carbon fiber and its resin matrix and the impregnation of carbon fiber in the matrix affecting porosity. The conventional carbon fiber composite materials can be classified into thermosetting composite materials using unsaturated polyester or epoxy as a resin matrix and thermoplastic composite materials using thermoplastic polymer resins such as polyolefin or polyamide (Nylon 6) as a resin matrix.

The thermosetting composite materials using unsaturated polyester or epoxy as a resin matrix can provide an excellent strength to the final composite material product but have disadvantages of uneasiness in handling the material and requiring setting process which takes relatively long time. To overcome the disadvantages above, a technique using a prepreg or the like has been tried but there is still a problem of difficulty in recycling.

On the other hand, the thermoplastic resin composite materials favor fast molding of composite material without requiring setting process, unlike the thermosetting resin, and can be welded and recycled. In particular, among those thermoplastic resins, polyamide-6, that is Nylon-6, displays excellent mechanical properties and relatively high thermostability, compared with other thermoplastic resins, in addition to the advantage of easy synthesis by ring-opening polymerization of monomers not by condensation reaction.

Even though the thermoplastic resin based carbon fiber composite material has been approved with good processability, recyclability and low costs, compared with the thermosetting resin based composite material, it has not been considered as a structural material. One of the reasons is that the thermoplastic resin based composite material does not show sufficient mechanical properties as an automotive structural material, which is attributed to poor interfacial adhesion between the carbon fiber reinforced material and the thermoplastic resin. The poor interfacial adhesion results in the reduction of the physical properties of the structural material due to deterioration of interfacial strength, for example it results in the reduction of tensile strength, compressive strength and interlaminar shear stress. Therefore, the interfacial adhesion between the carbon fiber reinforced material and the thermoplastic resin is a very important factor, so that numbers of researchers have been studied the relation between the carbon fiber and the thermoplastic resin matrix.

Recently, reactive molding processing gets a lot of attention as a method of high speed molding of thermoplastic resin composite materials. In the conventional method, a polymer resin is melted by heating and impregnated with carbon fiber. In the reactive molding process, a monomer having a low viscosity is impregnated efficiently in carbon fiber and polymerized through a reaction. This method is more excellent in impregnation property than the conventional method, and thus has the effect of improving interfacial adhesion and reducing porosity, so that it is possible to speed up the production of the composite material having excellent physical properties.

As a conventional technique for improving interfacial adhesion between thermoplastic polymer resin and carbon fiber, Korean Patent Publication No. 10-1498559 describes a method using a polymer matrix and multiple carbon fibers in the polymer matrix above, in which the surface of the carbon fibers has been coated with polydopamine. However, in this method, a polymer resin is melted by heating and impregnated with carbon fibers as described above, indicating that it does not provide an efficient method to improve physical properties through the improvement of interfacial adhesion nor provide a high speed molding.

Thus, the present inventors have studied a thermoplastic resin based carbon fiber composite material with improved interfacial adhesion. At last, the present inventors developed a sizing agent for carbon fiber useful for the reinforcement of interfacial adhesion between carbon fiber and thermoplastic composite material, a production method of a carbon fiber with improved interfacial adhesion using the same, a polymerization reaction type carbon fiber-reinforced polymer composite material using the carbon fiber with improved interfacial adhesion, and a production method thereof, leading to the completion of the present invention.

SUMMARY OF THE INVENTION

It is an object of the present invention to provide a sizing agent for carbon fiber useful for the reinforcement of interfacial adhesion, a production method of a carbon fiber with improved interfacial adhesion using the same, a polymerization reaction type carbon fiber-reinforced polymer composite material using the carbon fiber with improved interfacial adhesion, and a production method thereof To achieve the above object, the present invention provides a sizing agent for carbon fiber comprising a compound represented by formula 1 below and a phenoxy resin.

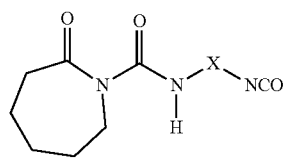

<Formula 1>

In formula 1, X is a $C_2$-$C_{20}$ aliphatic, aromatic, alicyclic, or aromatic aliphatic hydrocarbon.

The present invention also provides a sizing agent for carbon fiber prepared by urethane bond formation between a compound represented by formula 1 below and a hydroxy group of a phenoxy resin.

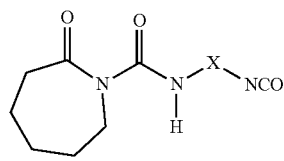

<Formula 1>

In formula 1, X is a $C_2$-$C_{20}$ aliphatic, aromatic, alicyclic, or aromatic aliphatic hydrocarbon.

The present invention also provides a production method of a sizing agent for carbon fiber comprising the steps of preparing a block isocyanate compound by reacting ε-caprolactam with one of two isocyanate groups of a diisocyanate compound as shown in reaction formula 1 below; and preparing a phenoxy resin modified with caprolactam by reacting the remaining isocyanate group of block isocyanate with a hydroxy group of a phenoxy resin.

<Reaction Formula 1>

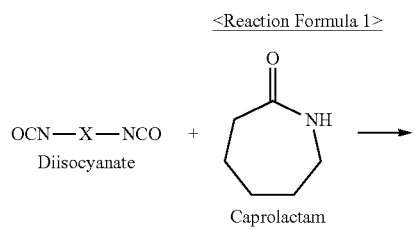

Diisocyanate

Caprolactam

-continued

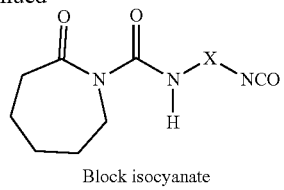

Block isocyanate

In reaction formula 1, X is a $C_2$-$C_{20}$ aliphatic, aromatic, alicyclic, or aromatic aliphatic hydrocarbon.

The present invention also provides a carbon fiber with improved interfacial adhesion, which is surface treated with the sizing agent for carbon fiber above.

The present invention also provides a carbon fiber with improved interfacial adhesion; and a carbon fiber reinforced polymer composite material comprising a polymer matrix containing the carbon fiber above as a reinforcement.

The present invention also provides a production method of a polymerization reaction type carbon fiber-reinforced polymer composite material comprising the steps of surface-treating a carbon fiber with a sizing agent for carbon fiber; impregnating a monomer in which ε-caprolactam is impregnated in the carbon fiber surface-treated with the sizing agent above; and polymerizing a monomer in which the impregnated ε-caprolactam is polymerized.

Advantageous Effect

The sizing agent for carbon fiber, the production method of a carbon fiber with improved interfacial adhesion, the polymerization reaction type carbon fiber-reinforced polymer composite material using the carbon fiber with improved interfacial adhesion and the production method of the same according to the present invention can improve interfacial adhesion between the carbon fiber and the resin.

According to the present invention, the impregnation of a carbon fiber can be increased, so that the pores formed in the inside of the carbon fiber reinforced polymer composite material product can be minimized, leading to the increase of strength.

Unlike the conventional method using a thermosetting resin based composite material, the method of the present invention facilitates the efficient production of a thermoplastic resin based composite material which does not require an additional setting process and has an advantage of welding and recycling by using the thermoplastic composite material.

The polymerization reaction based carbon fiber reinforced polymer composite material and the production method of the same according to the present invention demonstrates an excellent impregnation and favors a high speed molding because a monomer with a low viscosity is impregnated in the carbon fiber and polymerized through a reaction, unlike the conventional method wherein a thermoplastic resin is melted first and then impregnated in the carbon fiber.

DESCRIPTION OF THE PREFERRED EMBODIMENTS

Figure 1:
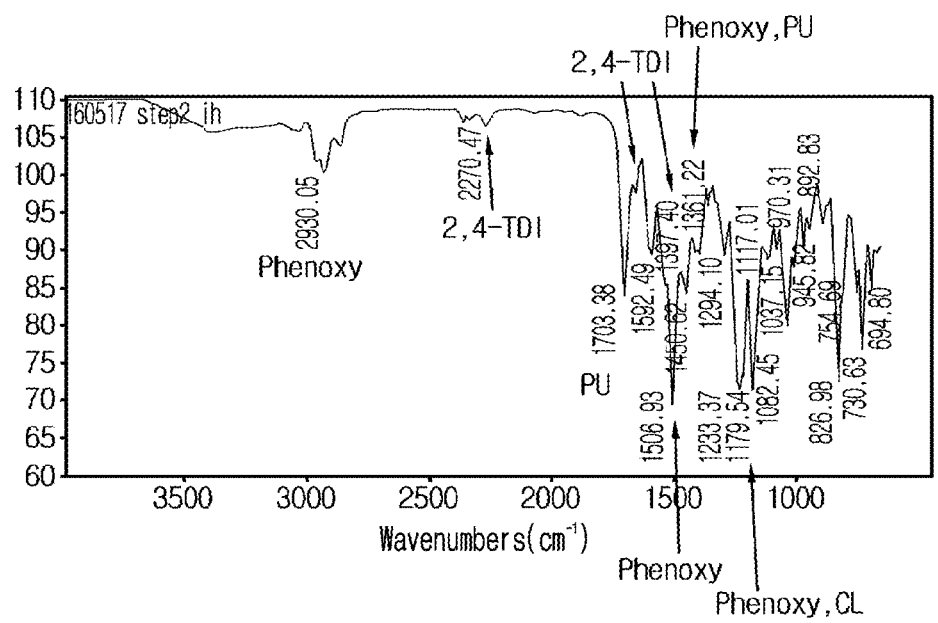
FIG. 1 shows the FTIR spectrum of a sizing agent for carbon fiber according to an embodiment of the present invention.

Hereinafter, the present invention is described in detail.

The terms or words used in this description and claims are not limited to ordinary or dictionary meaning and can be interpreted as a meaning and notion in relation to the technical idea of the present invention, based on the principles that the terms can be defined properly to describe the present invention in the best way. In addition, the term "contain" an element in this description indicates including other elements additionally not excluding other elements, unless specifically stated otherwise.

The present invention provides a sizing agent for carbon fiber comprising a compound represented by formula 1 below and a phenoxy resin.

<Formula 1>

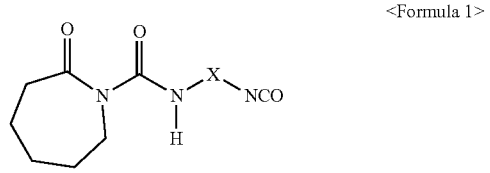

In formula 1, X is a $C_2$-$C_{20}$ aliphatic, aromatic, alicyclic, or aromatic aliphatic hydrocarbon.

In the sizing agent for carbon fiber of the present invention, the compound represented by formula 1 is preferably included at the concentration appropriate for the reaction with a hydroxy group included in the phenoxy resin. More preferably, the ratio of the compound represented by formula 1 and the phenoxy resin is 2:1, but the amount of the compound represented by formula 1 can be increased higher than the equivalent of —OH group included in the phenoxy resin.

The chemical structure of the phenoxy resin according to the present invention is shown in formula 2 below. The phenoxy resin preferably has a molecular weight of 25,000 to 60,000 g/mol and n is 88 to 211, and the content of —OH group therein is preferably OH(EW) 130 to 405 mg KOH/g, which would be converted into $2.32 \times 10^{-3}$ to $7.22 \times 10^{-3}$ —OH mol/(phenoxy resin g). Phenoxy resin has excellent adhesive strength, and accordingly demonstrates excellent interfacial adhesion between a carbon fiber and a polymer resin. Therefore, a carbon fiber sizing agent comprising the phenoxy resin can increase the interfacial adhesion between a carbon fiber and a polymer resin.

<Formula 2>

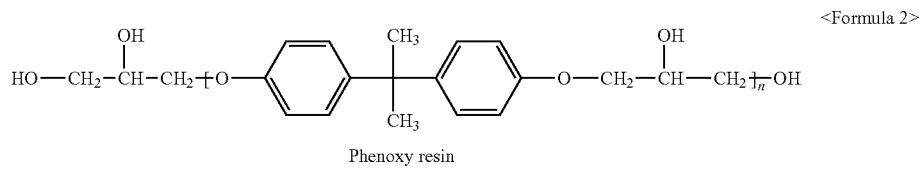

Phenoxy resin

The present invention also provides a sizing agent for carbon fiber prepared by urethane bond formation between a compound represented by formula 1 below and a hydroxy group of a phenoxy resin.

<Formula 1>

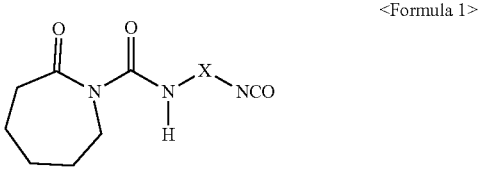

In formula 1, X is a $C_2$-$C_{20}$ aliphatic, aromatic, alicyclic, or aromatic aliphatic hydrocarbon.

The present invention also provides sizing agent for carbon fiber prepared by urethane bond formation between a block isocyanate compound prepared according to reaction formula 1 below and a hydroxy group of a phenoxy resin.

<Reaction Formula 1>

OCN—X—NCO    +    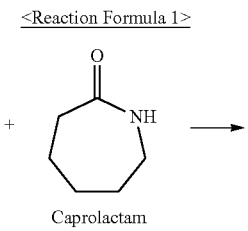
Diisocyanate                    Caprolactam

-continued

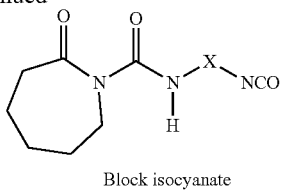

Block isocyanate

In reaction formula 1, X is a $C_2$-$C_{20}$ aliphatic, aromatic, alicyclic, or aromatic aliphatic hydrocarbon.

According to an embodiment of the present invention, the diisocyanate above is preferably toluene-2,4-diisocyanate ($CH_3C_6H_3$ $(NCO)_2$) (2,4-TDI).

The present invention also provides a production method of a sizing agent for carbon fiber comprising the steps of preparing a block isocyanate compound by reacting ε-caprolactam with one of two isocyanate groups of a diisocyanate compound as shown in reaction formula 1 below; and preparing a phenoxy resin modified with caprolactam by reacting the remaining isocyanate group of block isocyanate with a hydroxy group of a phenoxy resin.

<Reaction Formula 1>

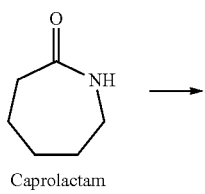

Diisocyanate   Caprolactam

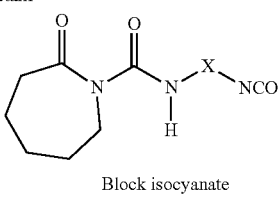

Block isocyanate

In reaction formula 1, X is a $C_2$-$C_{20}$ aliphatic, aromatic, alicyclic, or aromatic aliphatic hydrocarbon.

The reaction to produce a phenoxy resin modified with caprolactam by reacting the remaining isocyanate group of block isocyanate with a hydroxy group of a phenoxy resin is described by reaction formula 2 below.

<Reaction Formula 2>

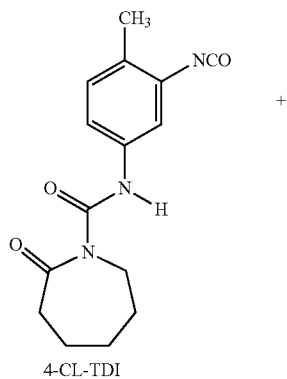

4-CL-TDI

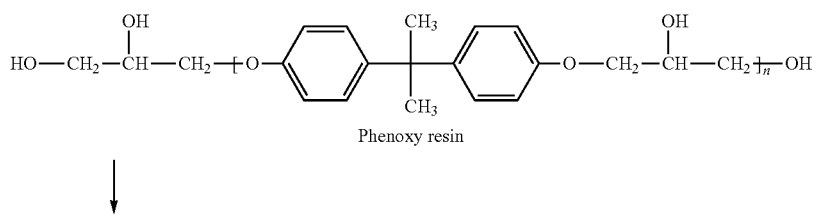

Phenoxy resin

↓

-continued

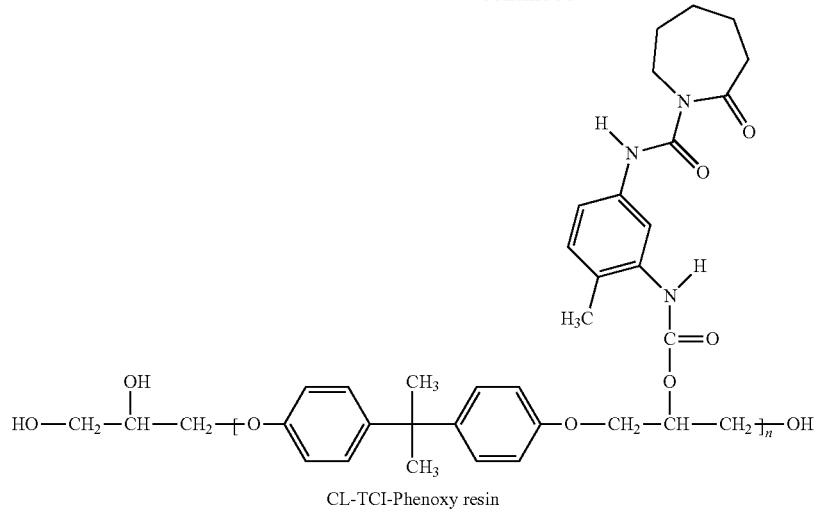

CL-TCI-Phenoxy resin

In reaction formula 2, the reaction between the remaining isocyanate group of block isocyanate (4-CL-TDI) according to the present invention and the tertiary hydroxy group located in the middle of molecular chain of the phenoxy resin is shown as an example. However, according to the mixing ratio of the block isocyanate and the phenoxy resin in the course of the reaction, an additional reaction with the first and secondary hydroxy group of the phenoxy resin and the concentration thereof can be regulated. At this time, as the ratio of the block isocyanate to the phenoxy resin increases, the effect of a sizing agent becomes more efficient. Preferably, the ratio of the block isocyanate (4-CL-TDI) to the phenoxy resin for the reaction is 2:1.

In this invention, the diisocyanate compound can be an aliphatic, aromatic, alicyclic or aromatic aliphatic compound which can contain two isocyanate groups in its molecular structure.

In this invention, the diisocyanate compound can be one or more aliphatic isocyanates selected from the group consisting of ethylene diisocyanate, trimethylene diisocyanate, tetramethylene diisocyanate, hexamethylene diisocyanate (HDI), octamethylene diisocyanate, nonamethylene diisocyanate, dodecamethylene diisocyanate, 2,2-dimethylpentane diisocyanate, 2,2,4-trimethylhexamethylene diisocyanate, decamethylene diisocyanate, butane diisocyanate, 1,3-butadiene-1,4-diisocyanate, 2,4,4-trimethylhexamethylene diisocyanate, 1,6,11-undecane triisocyanate, 2,2,4-trimethylhexamethylene diisocyanate, lysine diisocyanate, 2,6-diisocyanatemethylcaproate, bis(2-isocyanateethyl)fumarate, bis(2-isocyanateethyl) carbonate, 2-isocyanateethyl-2,6-diisocyanatehexanoate, 1,3,6-hexamethylene triisocyanate, 1,8-diisocyanato-4-isocyanatomethyloctane, 2,5,7-trimethyl-1,8-diisocyanato-5-isocyanatomethyloctane, bis(isocyanatoethyl) carbonate, bis(isocyanatoethyl)ether, 1,4-butyleneglycoldipropylether-diisocyanate, lysinediisocyanatomethylester, lysinetriisocyanate, 2 isocyanatoethyl-2,6-diisocyanatoethyl-2,6-diisocyanatohexanoate, and 2-isocyanatopropyl-2,6-diisocyanatohexanoate.

In this invention, the diisocyanate compound can be one or more aromatic isocyanates selected from the group consisting of 1,3-phenylene diisocyanate ($C_6H_4(NCO)_2$), 1,4-phenylene diisocyanate ($C_6H_4(NCO)_2$), toluene-2,4-diisocyanate ($CH_3C_6H_3(NCO)_2$), toluene-2,6-diisocyanate ($CH_3C_6H_3(NCO)_2$), toluene-2,5-diisocyanate ($CH_3C_6H_3(NCO)_2$), toluene-3,5-diisocyanate ($CH_3C_6H_3(NCO)_2$), 1,3-dimethylbenzene-2,4-diisocyanate (($CH_3)_2C_6H_2$ $(NCO)_2$), 1,3-methylbenzene-4,6-diisocyanate(($CH_3)_2C_6H_2$ $(NCO)_2$), 1,4-methylbenzene-2,5-diisocyanate(($CH_3)_2C_6H_2$ $(NCO)_2$), 1-ethylbenzene-2,4-diisocyanate ($C_2H_5.C_6H_3(NCO)_2$), 1-isopropylbenzene-2,4-diisocyanate (i-$C_3H_7C_6H_3$ $(NCO)_2$), 1-chlorobenzene-2,4-diisocyanate ($ClC_6H_3$ $(NCO)_2$), 1-nitrobenzene-2,4-diisocyanate ($O_2NC_6H_3$ $(NCO)_2$), 1-methoxybenzene-2,4-diisocyanate ($CH_3OC_6H_3$ $(NCO)_2$), 1-methoxybenzene-2,5-diisocyanate ($CH_3OC_6H_3$ $(NCO)_2$), 1-ethoxybenzene-2,4-diisocyanate ($C_2H_5OC_6H_3$ $(NCO)_2$), azobenzene-4,4'-diisocyanate ($OCNC_6H_4N=NC_6H_4NCO$), diphenylether-4,4'-diisocyanate ($OCNC_6H_4OC_6H_4NCO$), naphthalene-1,4-diisocyanate ($C_{10}H_6$ $(NCO)_2$), naphthalene-1,5-diisocyanate ($C_{10}H_6$ $(NCO)_2$), naphthalene-2,6-diisocyanate ($C_{10}H_6$ $(NCO)_2$), naphthalene-2,7-diisocyanate ($C_{10}H_6$ $(NCO)_2$), biphenyl-4,4'-diisocyanate ($OCNC_6H_4C_6H_4NCO$), 3,3'-dimethyl-biphenyl-4,4'-diisocyanate ([$OCN(CH_3)$ $C_6H_3-]_2$), 3,3'-dimethoxybiphenyl-4,4'-diisocyanate ([$OCN(CH_3O)C_6$ $H_3-]_2$), diphenylmethane-4,4'-diisocyanate ($OCNC_6H_4CH_2C_6H_4NCO$), diphenyldimethylmethane-4,4'-diisocyanate (($CH_3)_2C$ [$C_6H_4NCO]_2$), benzophenone-3,3'-diisocyanate ($OC[C_6H_4NCO]_2$), fluorene-2,7-diisocyanate ($C_{13}H_8$ $(NCO)_2$), anthraquinone-2,6-diisocyanate ($C_{14}H_6O_2$ $(NCO)_2$), 9-ethylcarbazole-3,6-diisocyanate ($C_{14}H_{11}N$ $(NCO)_2$), pyrene-3,8-diisocyanate ($C_{16}H_8$ $(NCO)_2$), and chrysene-2,8-diisocyanate ($C_{18}H_{10}$ $(NCO)_2$).

The present invention also provides a carbon fiber with improved interfacial adhesion, which is surface-treated with the sizing agent for carbon fiber above.

The carbon fiber of the present invention can be surface-treated with the mixture of the compound represented by formula 1 and the phenoxy resin, or with the reactant of the compound represented by formula 1 and the phenoxy resin.

The present invention also provides a carbon fiber reinforced polymer composite material comprising a carbon fiber with improved interfacial adhesion; and a polymer matrix containing the carbon fiber above as a reinforcement.

In this invention, the polymer matrix can be polyamide. The carbon fiber can be in the form of a dispersion comprising multiple monofilaments or a fibrous assembly selected from the group consisting of plain-woven, knit, braid, non-woven, satin, warp sating and twill.

The present invention also provides a production method of a polymerization reaction type carbon fiber-reinforced polymer composite material comprising the steps of surface-treating a carbon fiber with a sizing agent for carbon fiber; impregnating a monomer in which ε-caprolactam is impregnated in the carbon fiber surface-treated with the sizing agent above; and polymerizing a monomer in which the impregnated ε-caprolactam is polymerized.

In the step of polymerizing a monomer in this invention, the sizing agent coated on the surface of the carbon fiber plays a role of an initiator to induce polymerization of ε-caprolactam or an additional initiator can be added to induce the polymerization of ε-caprolactam.

Figure 3:
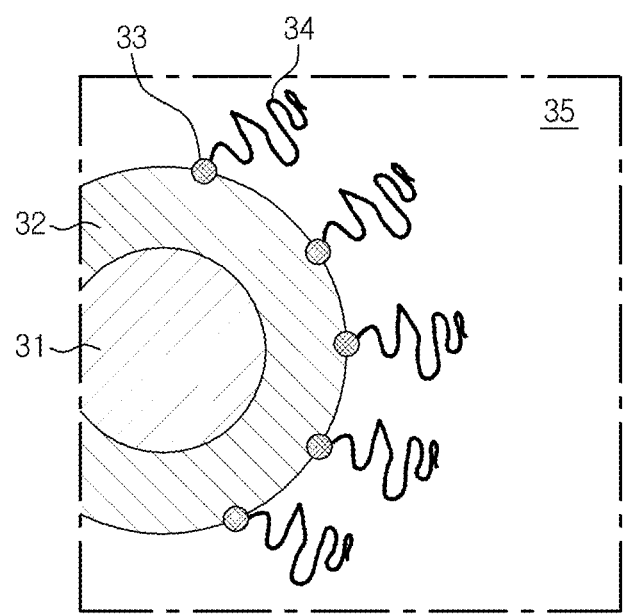
FIG. 3 is a conceptual diagram illustrating the improvement of surface adhesion between the carbon fiber treated with the sizing agent of the present invention and a polymer resin matrix according to an embodiment of the present invention.

Particularly, referring to FIG. 3, the polymerization of caprolactam is initiated by the sizing agent coated on the carbon fiber or the additional initiator, in which the polymer polymerized in the sizing agent coated on the carbon fiber binds to the sizing agent through covalent bond to form a strong interfacial adhesion. At this time, the sizing agent modifies the surface characteristics of the carbon fiber so that the interfacial adhesion can be improved, compared with the conventional carbon fiber using an additional initiator for the polymerization, and further demonstrates better linkage of the polymerized polymer due to the same chemical structure.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Preparative Example 1: Preparation of Block Isocyanate (4-CL-TDI)

First, the reaction of producing the block isocyanate according to an embodiment of the present invention is shown in reaction formula 1 below.

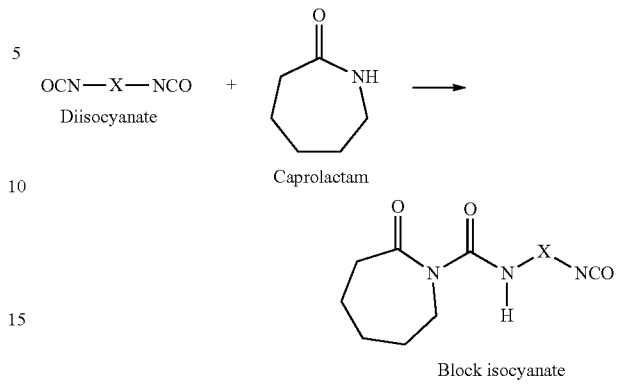

5.13 g of 2,4-toluenediisocyanate (2,4-TDI, Sigmaaldrich Inc.) was added to a three-necked flask, which was heated at 80° C. in of nitrogen and argon atmosphere. A caprolactam solution was prepared by dissolving 3.33 g of caprolactam in 10 g of cyclohexanone. The prepared caprolactam solution was added to the flask drop by drop. After the addition of caprolactam was completed, the reaction was continued for at least 12 hours to prepare a block isocyanate (4-CL-TDI) solution.

Preparative Example 2: Preparation of Sizing Agent for Carbon Fiber: Phenoxy Resin Modified with Caprolactam (CL-TDI Phenoxy Resin)

Next, the reaction of preparing the phenoxy resin modified with caprolactam by reacting the remaining isocyanate group of the block isocyanate prepared in Preparative Example 1 with a hydroxyl group of the phenoxy resin is shown in reaction formula 2 below.

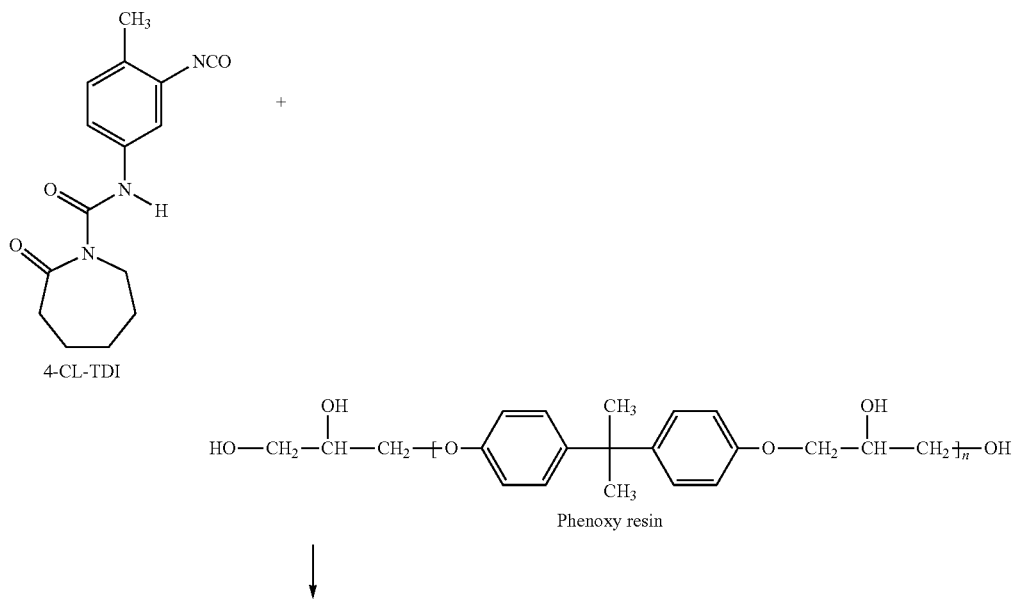

-continued

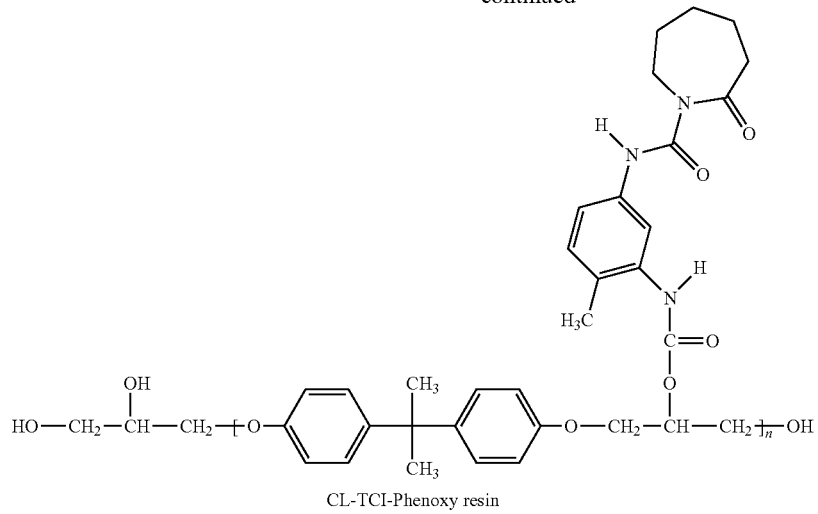

CL-TCI-Phenoxy resin 2.5 g of phenoxy resin (PKHA, InChem Corp., —OH e.g. 284 mg KOH/g on solid, $5.062\times10^{-3}$ mol/g) phenoxy resin was dissolved in 50 g of cyclohexanone (SAMCHUN chemical/Shinyo Pure Chemical Co., Ltd.), resulting in the 5 weight % solution. The prepared solution was heated at 80° C. 7.27 g of the block isocyanate (4-CL-TDI) solution prepared in Preparation Example 1 was added thereto drop by drop at the concentration of 2 times equivalent. One hour later, all the reactants were collected, followed by precipitation in excessive toluene. The compound obtained through filtering was vacuum-dried at room temperature to prepare a caprolactam-modified phenoxy resin (CL-TDI Phenoxy resin). The chemical structure of the caprolactam-modified phenoxy resin prepared above was confirmed by FTIR analysis (2930 $cm^{-1}$: —$CH_2$, —$CH_3$, bonded OH in carboxylic acid, 2270 $cm^{-1}$: —CN, —NCO, 1700 $cm^{-1}$: ester (—COO—), ketone(—CO—), —CHO, —COOH, 1592 $cm^{-1}$: —COO—, benzene ring, 1507 $cm^{-1}$: benzene ring, 1397 $cm^{-1}$: —COO—, —CH=$CH_2$, 1361 $cm^{-1}$: —C—$CH_3$, CO=, 1180 $cm^{-1}$: ester (—COO—), phenol), and the resultant FTIR absorption spectrum was shown in FIG. 1. The production of the phenoxy resin modified with caprolactam, the sizing agent for carbon fiber, (CL-TDI Phenoxy resin) was confirmed by confirming the characteristic peaks of the reactants caprolactam, phenoxy resin and 2,4-toluenediisocyanate and the urethane bond, which is an additional chemical bond, in the product.

Example 1: Preparation of Carbon Fiber Surface-Treated with Sizing Agent

The block isocyanate (4-CL-TDI) prepared in Preparative Example 1 was simply mixed with phenoxy resin. A TR30 (MITSUBISHI RAYON CO., LTD.) sheet prepared in the form of a plain-woven fabric was coated with the sizing agent by dipping the sheet in the sizing agent solution (0.5 weight % of block isocyanate (4-CL-TDI)/phenoxy resin mixture, 99.5 weight % of cyclohexane/tetrahydrofuran (1:1) mixture). The coated sizing agent was dried in a convection oven at 60° C. for 2 hours, resulting in the preparation of a carbon fiber surface-treated with the sizing agent.

Example 2: Preparation of Carbon Fiber Surface-Treated with Sizing Agent

A TR30 (MITSUBISHI RAYON CO., LTD.) sheet prepared in the form of a plain-woven fabric was coated with the sizing agent by dipping the sheet in the sizing agent solution (0.5 weight % of the sizing agent for carbon fiber (a chemical reactant of the block isocyanate (4-CL-TDI) prepared according to the Preparative Example 2 and phenoxy resin), 99.5 weight % of cyclohexane/tetrahydrofuran (1:1) mixture). The coated sizing agent was dried in a convection oven at 60° C. for 2 hours, resulting in the preparation of a carbon fiber surface-treated with the sizing agent.

Figure 2:
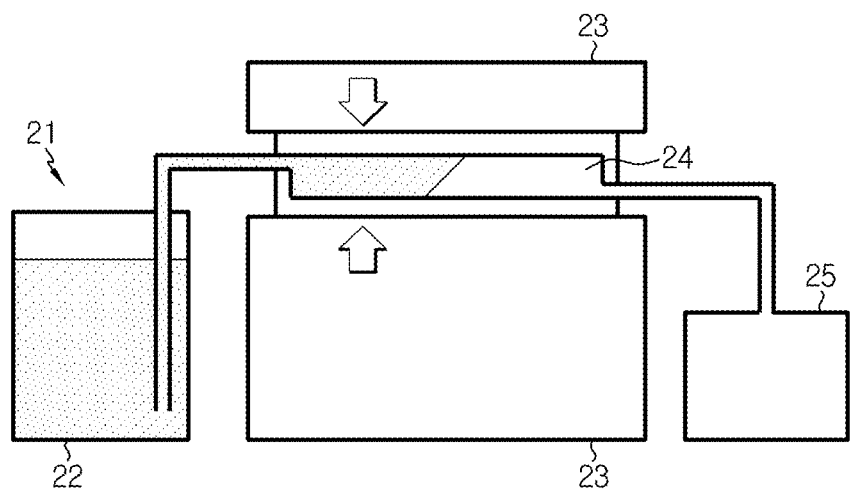
FIG. 2 is a conceptual diagram illustrating the equipment for producing a polymerization reaction type carbon fiber-reinforced polymer composite material according to an embodiment of the present invention.

Preparative Example 3: Preparation of Carbon Fiber-Reinforced Polymer Composite Material A carbon fiber-reinforced polymer composite material was prepared by polymerization of ε-caprolactam in the presence of ε-caprolactam monomers and a catalyst in the carbon fiber surface-treated with the sizing agents prepared in Example 1 and Example 2. In addition, another carbon fiber-reinforced polymer composite material was prepared using the carbon fiber without surface treatment with the sizing agent of the present invention in Comparative Example 1. An apparatus for producing a polymerization reaction type carbon fiber-reinforced polymer composite material according to an embodiment of the present invention is schematically shown in FIG. 2. In the apparatus for producing a polymerization reaction type carbon fiber-reinforced polymer composite material, the melted caprolactam and the solution (22) prepared by dissolving an initiator and a catalyst separately supplied from the reactor (21) was supplied to the mold (24) positioned between the hot press (23) transferring the pressure and heat, and the air capable of generating air bubbles in the mold was eliminated by the vacuum pump (25). In addition, the concept of improving interfacial adhesion between resin and carbon fiber mediated by the sizing agent playing a role as a reaction initiator is illustrated in FIG. 3.

The method above is illustrated in more detail hereinafter. A carbon fiber was layered in the mold equipped in the hot press (23), followed by heating. Caprolactam, an additional initiator and a catalyst were all dissolved in a separate reactor (21) and the prepared mixed solution (22) was provided to the mold (24). The carbon fiber was impregnated in the solution and reaction was induced by the heat in the mold, leading to polymerization. Then, the carbon fiber-reinforced polymer composite material was prepared by demolding the composite material from the mold. At this time, as shown in FIG. 3, the phenoxy resin (32) of the sizing agent was located on the surface of the carbon fiber (31) and the block isocyanate (4-Cl-TDI) included in the phenoxy resin began to act as an initiator (33) to induce the polymerization of caprolactam, resulting in the formation of polyamide-6 (34) growing from the phenoxy resin. Separately, the initiator induced the polymerization of caprolactam to form polyamide-6 (35) capable of forming another matrix outside the carbon fiber treated with the sizing agent. At this time, the polymer polymerized in the sizing agent coated on the carbon fiber was combined with the sizing agent through covalent bond to form strong interfacial adhesion. Since the sizing agent modified the surface properties of the carbon fiber, the polymer polymerized by the separate initiator also formed improved interfacial adhesion with the carbon fiber, compared with the conventional polymer. In addition, the chemical structure was the same between the polymerized polymers, so that they were well combined with each other.

Analytical Example 1: Shear Test of Carbon Fiber-Reinforced Polymer Composite Material Shear test (ILSS, ASTM-D2344) was performed to confirm the interfacial adhesion of the carbon fiber-reinforced polymer composite material prepared according to Preparation Example 3 of the present invention using the carbon fibers of Example 1, Example 2 and Preparative Example 1. The size of the specimen was as follows: specimen length=thickness×6, specimen width=thickness×2. The total thickness was 3.2 mm. The test speed was set at a crosshead speed of 1.0 mm/min.

Figure 4A:
FIG. 4 is a set of photographs illustrating the shapes of a composite material specimen and the states thereof before and after the test according to an embodiment of the present invention.
Figure 4B:
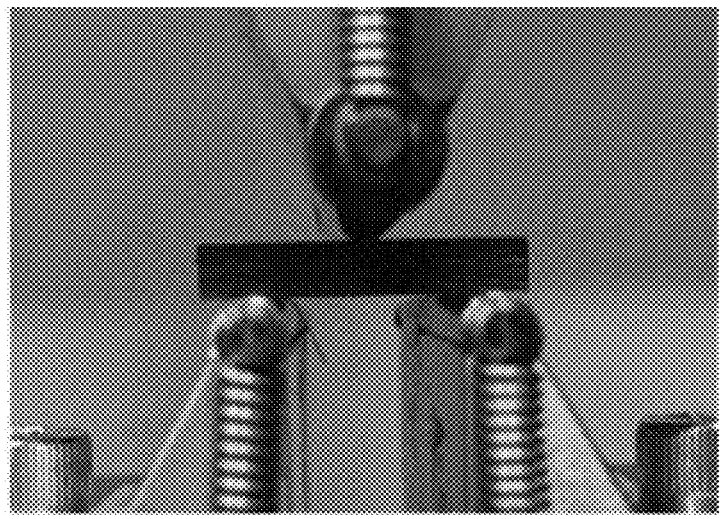
Figure 4C:
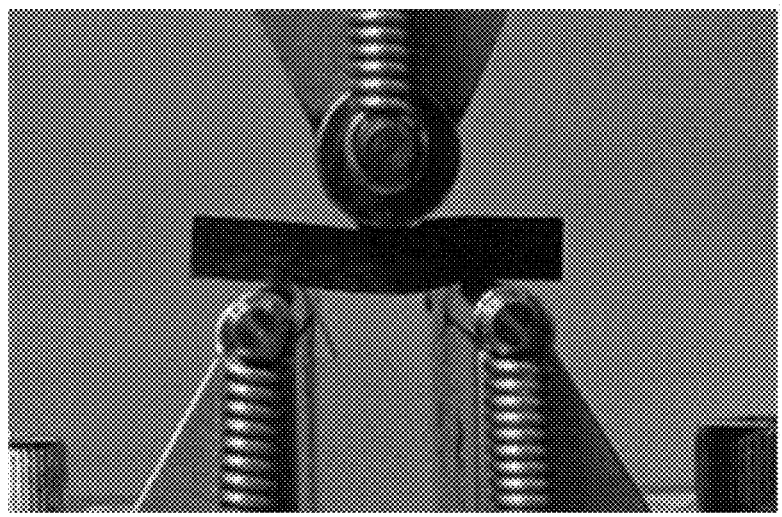
Figure 6:
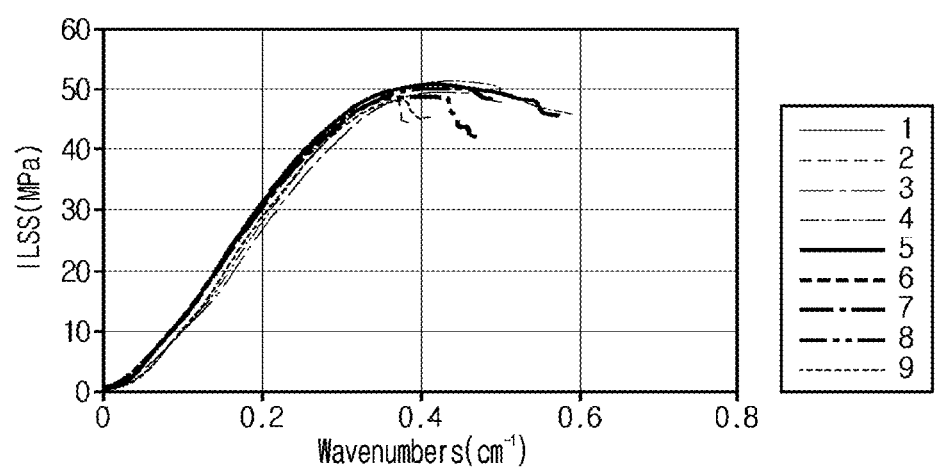
FIG. 6 is a graph illustrating the results of shear test of the composite material according to an embodiment of the present invention.

FIG. 4 is a set of photographs illustrating the shapes of a composite material specimen prepared according to Example 1 of the present invention and the states thereof before and after the test. FIG. 4(a) is the shape of the specimen after the specimen processing and after the test, FIG. 4(b) is the shape before the test, and FIG. 4(c) is the shape after the test. Table 1 below shows the test results of the composite material prepared according to Example 1, and FIG. 6 is a graph presenting the test results.

TABLE 1

| Specimen No. | Width (mm) | Thickness (mm) | Max load (N) | Strength (MPa) |
| --- | --- | --- | --- | --- |
| 1 | | | | |
| 2 | 6.63 | 3.36 | 1460.00 | 49.10 |
| 3 | 6.63 | 3.35 | 1476.00 | 49.80 |
| 4 | 6.62 | 3.40 | 1544.00 | 51.50 |
| 5 | 6.65 | 3.38 | 1527.00 | 51.00 |
| 6 | 6.63 | 3.36 | 1469.00 | 49.50 |
| 7 | 6.64 | 3.34 | 1486.00 | 50.20 |
| 8 | 6.61 | 3.38 | 1459.00 | 49.00 |
| 9 | 6.63 | 3.34 | 1426.00 | 48.30 |
| Ave. | 6.63 | 3.36 | 1480.88 | 49.80 |
| St. Dev. | 0.010 | 0.019 | 38.227 | 1.066 |
| St. Dev(%) | 0.198 | 0.736 | 3.356 | 2.784 |

Figure 5A:
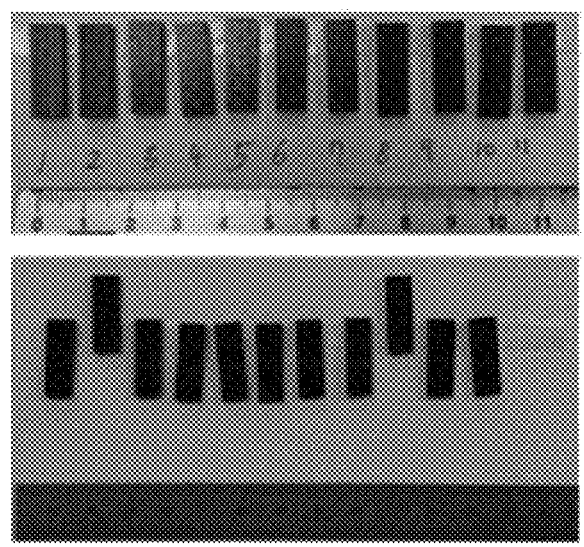
FIG. 5 is a set of photographs illustrating the shapes of a composite material specimen and the states thereof before and after the test according to an embodiment of the present invention.
Figure 5B:
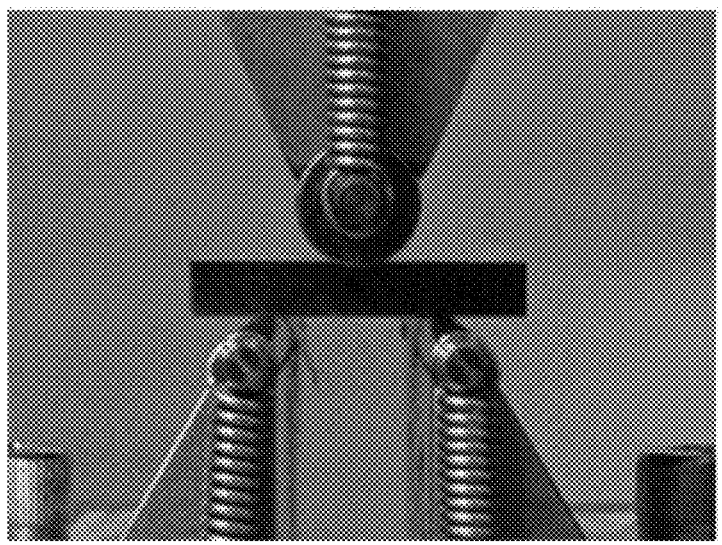
Figure 5C:
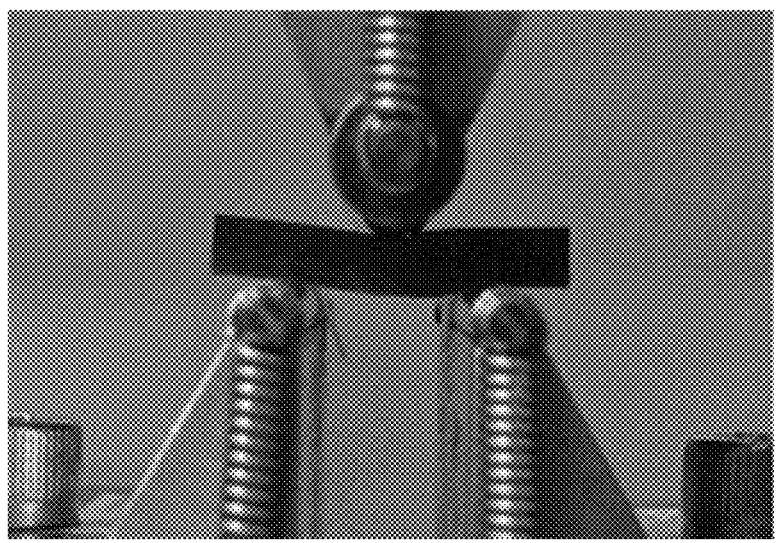
Figure 7:
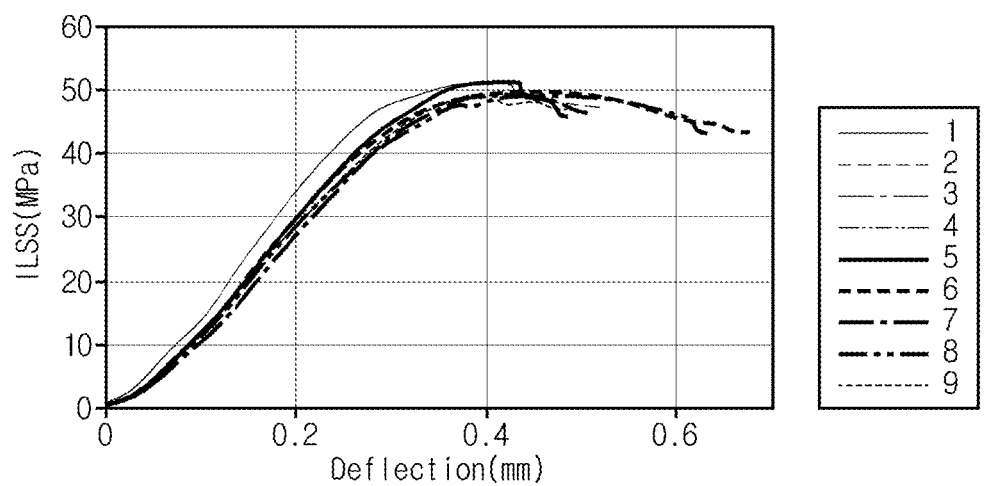
FIG. 7 is a graph illustrating the results of shear test of the composite material according to an embodiment of the present invention.

FIG. 5 is a set of photographs illustrating the shapes of a composite material specimen prepared according to Example 2 of the present invention and the states thereof before and after the test. FIG. 5(a) is the shape of the specimen after the specimen processing and after the test, FIG. 5(b) is the shape before the test, and FIG. 5(c) is the shape after the test. Table 2 below shows the test results of the composite material prepared according to Example 2, and FIG. 7 is a graph presenting the test results.

TABLE 2

| Specimen No. | Width (mm) | Thickness (mm) | Max load (N) | Strength (MPa) |
| --- | --- | --- | --- | --- |
| 1 | 6.72 | 3.31 | 1520.00 | 51.20 |
| 2 | 6.71 | 3.26 | 1430.00 | 49.00 |
| 3 | 6.73 | 3.30 | 1490.00 | 50.30 |
| 4 | 6.72 | 3.28 | 1442.00 | 49.00 |
| 5 | 6.72 | 3.31 | 1525.00 | 51.50 |
| 6 | 6.72 | 3.27 | 1466.00 | 50.00 |
| 7 | 6.72 | 3.30 | 1460.00 | 49.40 |
| 8 | 6.71 | 3.25 | 1436.00 | 49.40 |
| 9 | 6.71 | 3.25 | 1445.00 | 49.60 |
| Ave. | 6.72 | 3.28 | 1468.22 | 49.93 |
| St. Dev. | 0.007 | 0.023 | 35.668 | 0.910 |
| St. Dev(%) | 0.140 | 0.923 | 3.158 | 2.368 |

Figure 8:
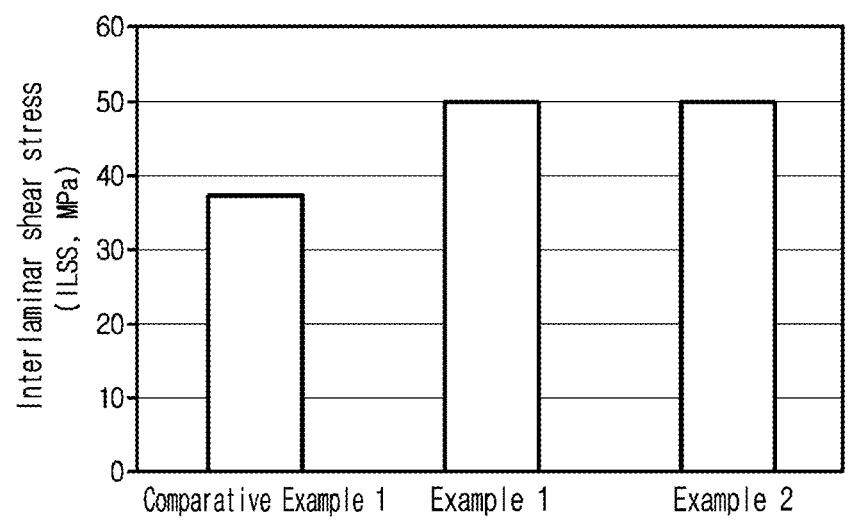
FIG. 8 is a graph illustrating the comparison of the results of shear test of the composite materials according to an embodiment of the present invention.

The results of the test above and the result of the interlaminar shear strength test performed in Comparative Example 1, are shown in FIG. 8. The ILSS shear strength of the composite material prepared by using the carbon fiber surface-treated with the sizing agent prepared by simply mixing block isocyanate (4-CL-TDI) and phenoxy resin of Example 1 was 49.8 MPa, and the ILSS shear strength of the composite material prepared by using the carbon fiber surface-treated with the sizing agent, the chemical reactant of block isocyanate (4-CL-TDI) and phenoxy resin of Example 2 was 49.9 MPa, proving the ILSS (interlaminar shear strength) between the two materials was similar. In the meantime, the ILSS (interlaminar shear strength) of the carbon fiber reinforced polymer composite material prepared by using the carbon fiber of Comparative Example 1 whose surface was not treated was 37.3 MPa.

The results above proved that the composite material prepared by using the carbon fiber surface-treated with the sizing agent prepared by using block isocyanate (4-CL-TDI) and phenoxy resin according to the present invention had significantly improved ILSS (interlaminar shear strength) of 33% or more as compared with the other composite materials prepared by using the conventional carbon fiber.

The ILSS (interlaminar shear strength) is a mechanical strength that is significantly affected by the interfacial adhesion between the fiber and the resin. Therefore, as shown in FIG. 3, it was confirmed that the sizing agent improved the interfacial adhesion by increasing the ILSS value.

What is claimed is:
1. A carbon fiber, which is surface-treated with a sizing agent for carbon fiber prepared by urethane bond formation between a compound represented by formula 1 below and a hydroxy group of a phenoxy resin:

<Formula 1>

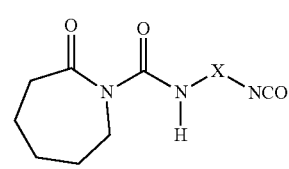

In Formula 1, X is a $C_2$-$C_{20}$ aliphatic, aromatic, alicyclic, or aromatic aliphatic hydrocarbon.

2. A carbon fiber according to claim 1, wherein the sizing agent is prepared according to production method comprising the following steps:

preparing a block isocyanate compound by reacting ε-caprolactam with one of two isocyanate groups of a diisocyanate compound as shown in Reaction Formula 1 below;

<Reaction Formula 1>

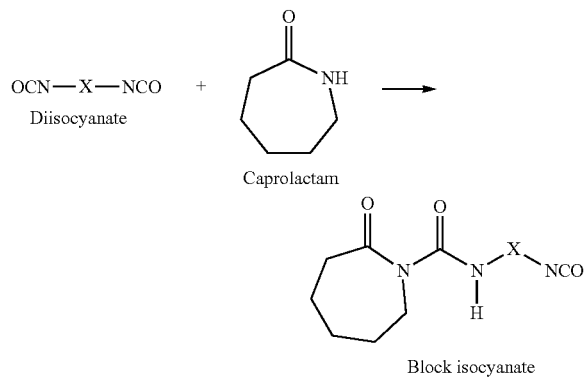

In Reaction Formula 1, X is a $C_2$-$C_{20}$ aliphatic, aromatic, alicyclic, or aromatic aliphatic hydrocarbon; and preparing a phenoxy resin modified with caprolactam by reacting the remaining isocyanate group of block isocyanate with a hydroxy group of a phenoxy resin.

3. A carbon fiber according to claim 2, wherein the diisocyanate compound is one or more aliphatic isocyanates selected from the group consisting of ethylene diisocyanate, trimethylene diisocyanate, tetramethylene diisocyanate, hexamethylene diisocyanate (HDI), octamethylene diisocyanate, nonamethylene diisocyanate, dodecamethylene diisocyanate, 2,2-dimethylpentane diisocyanate, 2,2,4-trimethylhexamethylene diisocyanate, decamethylene diisocyanate, butane diisocyanate, 1,3-butadiene-1,4-diisocyanate, 2,4,4-trimethylhexamethylene diisocyanate, 2,2,4-trimethylhexamethylene diisocyanate, lysine diisocyanate, 2,6-diisocyanatemethylcaproate, bis(2-isocyanateethyl)fumarate, bis(2-isocyanateethyl)carbonate, bis(isocyanatoethyl) carbonate, bis(isocyanatoethyl)ether, 1,4-butyleneglycoldipropylether-ω,ω'-diisocyanate, and lysinediisocyanatomethylester.

4. A carbon fiber according to claim 2, wherein the diisocyanate compound is one or more aromatic isocyanates selected from the group consisting of 1,3-phenylene diisocyanate ($C_6H_4(NCO)_2$), 1,4-phenylene diisocyanate ($C_6H_4(NCO)_2$), toluene-2,4-diisocyanate ($CH_3C_6H_3(NCO)_2$), toluene-2,6-diisocyanate ($CH_3C_6H_3(NCO)_2$), toluene-2,5-diisocyanate ($CH_3C_6H_3(NCO)_2$), toluene-3,5-diisocyanate ($CH_3C_6H_3(NCO)_2$), 1,3-dimethylbenzene-2,4-diisocyanate (($CH_3)_2C_6H_2(NCO)_2$), 1,3-methylbenzene-4,6-diisocyanate (($CH_3)_2C_6H_2(NCO)_2$), 1,4-methylbenzene-2,5-diisocyanate (($CH_3)_2C_6H_2(NCO)_2$), 1-ethylbenzene-2,4-diisocyanate ($C_2H_5.C_6H_3(NCO)_2$), 1-isopropylbenzene-2,4-diisocyanate (i-$C_3H_7C_6H_3(NCO)_2$), 1-chlorobenzene-2,4-diisocyanate ($ClC_6H_3(NCO)_2$), 1-nitrobenzene-2,4-diisocyanate ($O_2NC_6H_3(NCO)_2$), 1-methoxybenzene-2,4-diisocyanate ($CH_3OC_6H_3(NCO)_2$), 1-methoxybenzene-2,5-diisocyanate ($CH_3OC_6H_3(NCO)_2$), 1-ethoxybenzene-2,4-diisocyanate ($C_2H_5OC_6H_3(NCO)_2$), azobenzene-4,4'-diisocyanate ($OCNC_6H_4N=NC_6H_4NCO$), diphenylether-4,4'-diisocyanate ($OCNC_6H_4OC_6H_4NCO$), naphthalene-1,4-diisocyanate ($C_{10}H_6(NCO)_2$), naphthalene-1,5-diisocyanate ($C_{10}H_6(NCO)_2$), naphthalene-2,6-diisocyanate ($C_{10}H_6(NCO)_2$), naphthalene-2,7-diisocyanate ($C_{10}H_6(NCO)_2$), biphenyl-4,4'-diisocyanate ($OCNC_6H_4C_6H_4NCO$), 3,3'-dimethyl-biphenyl-4,4'-diisocyanate ([$OCN(CH_3)C_6H_3-]_2$), 3,3'-dimethoxybiphenyl-4,4'-diisocyanate ([$OCN(CH_3O)C_6H_3-]_2$), diphenyldimethylmethane-4,4'-diisocyanate (($CH_3)_2C[C_6H_4NCO]_2$), benzophenone-3,3'-diisocyanate ($OC[C_6H_4NCO]_2$), fluorene-2,7-diisocyanate ($C_{13}H_8(NCO)_2$), anthraquinone-2,6-diisocyanate ($C_{14}H_6O_2(NCO)_2$), 9-ethylcarbazole-3,6-diisocyanate ($C_{14}H_{11}N(NCO)_2$), pyrene-3,8-diisocyanate ($C_{16}H_8(NCO)_2$), and chrysene-2,8-diisocyanate ($C_{18}H_{10}(NCO)_2$).

5. A carbon fiber reinforced polymer composite material comprising the carbon fiber of claim 1; and a polymer matrix containing the carbon fiber above as a reinforcement.

6. The carbon fiber reinforced polymer composite material according to claim 5, wherein the carbon fiber is in the form of a dispersion comprising multiple monofilaments or a fibrous assembly selected from the group consisting of plain-woven, knit, braid, non-woven, satin, warp sating and twill.

7. The carbon fiber reinforced polymer composite material according to claim 5, wherein the polymer matrix is polyamide.

8. A production method of a carbon fiber-reinforced polymer composite material comprising the following steps:

surface-treating a carbon fiber with a sizing agent for carbon fiber prepared by urethane bond formation between a compound represented by formula 1 below and a hydroxy group of a phenoxy resin;

<Formula 1>

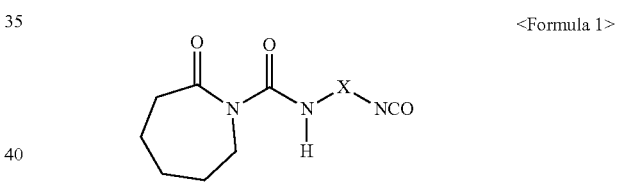

In formula 1, X is a $C_2$-$C_{20}$ aliphatic, aromatic, alicyclic, or aromatic aliphatic hydrocarbon;

impregnating a monomer in which ε-caprolactam is impregnated in the carbon fiber surface-treated with the sizing agent above; and polymerizing a monomer in which the impregnated ε-caprolactam is polymerized.

9. The production method of a carbon fiber-reinforced polymer composite material according to claim 8, wherein the step of polymerizing a monomer is accomplished by the sizing agent coated on the surface of the carbon fiber playing a role of an initiator to induce polymerization of ε-caprolactam.

10. The production method of a carbon fiber-reinforced polymer composite material according to claim 8, wherein the step of polymerizing a monomer is accomplished with ε-caprolactam by using an additional initiator.

11. The production method of a carbon fiber-reinforced polymer composite material according to claim 8, wherein the carbon fiber is in the form of a dispersion comprising multiple monofilaments or a fibrous assembly selected from the group consisting of plain-woven, knit, braid, non-woven, satin, warp sating and twill.

* * * * *